(12) United States Patent
Sands et al.

(10) Patent No.: US 6,673,746 B1
(45) Date of Patent: Jan. 6, 2004

(54) VIRULENCE ENHANCEMENT OF BIOHERBICIDES

(75) Inventors: David C. Sands, Bozeman, MT (US); Alice L. Pilgeram, Bozeman, MT (US); Timothy W. Anderson, Bozeman, MT (US); Kanat S. Tiourebaev, Almaty (KZ)

(73) Assignee: AG/Bio Con, Inc., Bozeman, MT (US)

( * ) Notice: Subject to any disclaimer, the term of this patent is extended or adjusted under 35 U.S.C. 154(b) by 204 days.

(21) Appl. No.: 09/748,644

(22) Filed: Jun. 25, 2001

Related U.S. Application Data

(60) Provisional application No. 60/172,771, filed on Dec. 20, 1999.

(51) Int. Cl.[7] ............................................. A01N 63/00
(52) U.S. Cl. ...................................................... 504/117
(58) Field of Search ......................................... 504/117

(56) References Cited

U.S. PATENT DOCUMENTS 5,538,890 A  *  7/1996  Sands et al. ............. 435/254.1

OTHER PUBLICATIONS

Tiourebaev et al. "Amino Acid Excretion Enhances Virulence of Bioherbicides". Proceedings of the X International Symposium on Biological Control of Weeds, Jul. 4–14, 1999, Montana State U. Bozeman, Montana.*

Adelberg, E. A., "Selected of Bacterial Mutants Which Excrete Antoagonists of Antimetabolites," *J. Bacteriol.* 76:326, 1958.

Bryan, J.K., "Synthesis of the Aspartate Family and Branched–Chain Amino Acids," In: *The Biochemistry of Plants*, Acad. Press, New York, London, 5:403–452, 1980.

Carlson, P. S., "The Use of Protoplasts for Genetic Research," *Proc. Nat. Acad. Sci.* 70:598–602, 1973.

Green, C. E., and Phillips, R. L., "Potential Selection System for Mutants with Increased Lysine, Threonine, and Methionine in Cereal Crops," *Crop. Sci.* 14:827–830, 1974.

Lucas, G. B., "Frenching," In: *Diseases of tobacco*. The Scarecrow Press, New York & London, pp. 478–485, 1965.

Maiti, S. N., et al., Effect of Valine and the Herbicide Sulfometuron Methyl on Acetolactate Synthase Activity in Nuclear and Plasmid–Borne Sulfometuron Methyl Resistant *Saccharomyces Cerevisiae* Strains, *Can. J. Microbiol.* 34:680–685, 1988.

Relton, J. M., et al., "Altered Feedback Sensitivity of Acethydroxyacid Synthase From Valine–Resistant Mutants of Tobacco (*Nicotiana tabacum L.*)," *Planta* 169;46–50, 1986.

Rosenthal, G. A., *Plant Nonprotein Amino and Imido Acids: Biological, Biochemical and Toxicological Properties*, Acad. Press, New York, London, pp. 57–157, 1982.

Sands and Zucker, "Amino Acid Inhibition of Pseudomonads and Its Reversal by Biosynthetically Related Amino Acids," *Physiological Plant Pathology* 9:127–133, 1976.

(List continued on next page.)

Primary Examiner—S. Mark Clardy
(74) Attorney, Agent, or Firm—Klarquist Sparkman LLP

(57) ABSTRACT

Disclosed are novel methodologies for virulence enhancement of fungal and bacterial pathogens for biological control of target plants. Described is a selection process for phytopathogenic microorganisms that excrete selected amino acids. Pathogenicity studies demonstrate that these amino acid-excreting plant pathogens show greater virulence against target plants than do corresponding wild type strains. Host range evaluations of these mutants did not reveal any increase of virulence towards non-target plants. This novel approach to enhancement of microbial herbicides can be used across a broad spectrum of microbial groups to improve the efficacy of bio-control. Also disclosed is the use of selected mutants of plant pathogenic microorganisms that overproduce one or more inhibitory amino acids to enhance control of target plants.

13 Claims, 1 Drawing Sheet

OTHER PUBLICATIONS

Steinberg, R. A., "A "Frenching" Response of Tobacco Seedlings to Isoleucine," *Science* 103:329–330, 1946.

Steinberg, R. A., et al., "Accumulation of Free Amino Acids as a Chemical Basis for Morphological Symptoms in Tobacco Manifesting Frenching and Mineral Deficiency Symptoms," *Plant Physiol.* 25:279–288, 1950.

Umbarger, E., and Davis, B., "Pathways of Amino Acid Biosynthesis," In: *The Bacteria. A Treatise on Structure and Function*, Academic Press, New York, London, 3:167–251, 1962.

Wu, K., et al., "A Valine–Resistant Mutant of *Arabiodopsis thaliana* Displays an Acetolactate Synthase with Altered Feedback Control," *Planta.* 192:249–255, 1994.

* cited by examiner

VIRULENCE ENHANCEMENT OF BIOHERBICIDES

PRIORITY CLAIM

This claims the benefit of U.S. Provisional Application No. 60/172,771, filed Dec. 20, 1999.

STATEMENT REGARDING FEDERALLY SPONSORED RESEARCH

The United States Government may have certain rights in this application pursuant to a non-competitive ARS Grant No. 58-1275-5-013, awarded by the USDA.

BACKGROUND

Most bioherbicides are developed from host-specific plant pathogens. These pathogens attack and suppress the growth and expansion of a target weed but are seldom virulent enough to effectively destroy the target plant. The approach we describe is a novel way to enhance the virulence of plant biocontrol agents without producing potentially dangerous metabolites. The basic background behind this study involves aspects of self-regulation of intermediary metabolism in plants and microbes. This approach does not require recombinant genetics thereby decreasing the time and testing involved with biosafety considerations.

Most modern chemical herbicides inhibit a single biosynthetic enzyme in the target plant. This enzyme inhibition renders the plant incapable of producing metabolites essential for plant growth or defense and eventually leads to death of the plant. Glyphosate, sulfonylureas, imidazolinones, 1, 2, 4-triasol and pyrimidines are classic examples of herbicides that interfere with amino acid biosynthesis. Glyphosate inhibits 5' enol pyruvyl shikimate 3-phosphate synthase (EPSP), the key enzyme in the shikimic acid pathway (Amrhein, 1986). Another target enzyme, acetolactate synthase (ALS) is a unique herbicide target in that several structurally differing compounds inhibit the enzyme (sulfonylureas, imidazolinones, 1, 2, 4-triasol pyrimidines). The activity of ALS is also inhibited by its own biosynthetic end-products (valine and/or isoleucine) efficiently regulating the balanced production of branched amino acids. Accumulation of a single end-product in a branched biosynthetic pathway may lead to shutdown of the entire pathway. For example, isoleucine inhibits ALS preventing not only biosynthesis of isoleucine but also biosynthesis of valine, leucine, and the essential vitamin, pantothenic acid. Accumulation of both isoleucine and valine has a synergistic effect further reducing the activity of the enzyme.

Feedback inhibition of biosynthetic enzymes in other amino acid pathways is also well documented. In higher plants and bacteria, lysine, threonine, and methionine are synthesized in a branched pathway from aspartate (Bryan, 1980; Umbarger and Davis, 1962). The activity of the first enzyme in this pathway (aspartate kinase) is regulated by the concentrations of lysine and threonine. The activity of the third enzyme in the pathway is regulated by the concentration of methionine (Green and Phillips, 1974). Hence, the exogenous application of one of the end-product amino acids leads to repression of the entire pathway, resulting in depletion of the other two amino acids, and eventual starvation.

Mis-regulation by exogenous end-products has been reported in the plant kingdom. Examples include "frenching disease" of tobacco where unusual strains of *Pseudomonas flourescens*, a bacterium in the root zone, produce a significant amount of the essential amino acid isoleucine, which inhibits the plant's growth (Steinberg, 1950, Steinberg, 1946). Among the earliest symptoms of frenching is chlorosis along the margins of young leaves, which spread gradually across the entire leaf surface. As the leaf develops, only the midrib elongates, thereby producing a distorted narrow leaf. Terminal growth is greatly retarded and apical dominance is lost, resulting in a stunted plant with small, distorted leaves. In severe cases, the axillary buds are stimulated into growth (Steinberg, 1950; Lucas, 1965). Steinberg (1950) reported Bacillus cereus also could cause severe "frenching" symptoms in tobacco seedlings. Higher populations of this nonpathogenic microorganism were found in the rhizosphere of frenched tobacco than in the rhizosphere of normal tobacco. High concentrations of free isoleucine were detected in the leaves of frenched plants (Steinberg, 1946).

Regulatory mutants that are resistant to feedback inhibition or enzyme repression have been reported in bacteria (Adelberg, 1958; Umbarger and Davis, 1962), in fungi (Maiti, 1988), and in plants (Wu et al, 1994; Relton et al, 1986, Carlson, 1973). The biosynthetic activities of these "mutant" enzymes were not sensitive to inhibitory concentrations of end-product resulting in continuous production of pathway intermediates and biosynthetic end-products. In bacteria, the accumulated end-product may be excreted from the cell, restoring the balance of the intracellular amino acid pool. This excretion of amino acids by a plant pathogenic bacterium or fungus could disrupt the delicately balanced production of amino acids in infected host plants further increasing the susceptibility to the pathogen or biological control agent.

In some cases, regulatory mutants can be selected by exposing the organism to high concentrations of a single amino acid and selecting for wild-type growth. An alternative approach is to expose the microorganism to lethal concentrations of a toxic amino acid analog. Amino acid analogs may act as false end-product inhibitors or as false repressors for enzymes involved in biosynthesis of amino acids (Rosenthal, 1982; Umbarger and Davis, 1962). In addition, amino acid analogs may be competitively incorporated into proteins altering or eliminating the protein activity. Strains may show resistance to these analogs by one of two ways: 1) they are incapable of taking up the toxic metabolite; or 2) they are insensitive to the regulatory effects of the toxic analog. The mutants that are insensitive to the regulatory effect of analogs are also resistant to the regulatory effect of the corresponding amino acid and may overproduce and therefore, excrete the amino acids end-products of the specific pathway.

MATERIALS AND METHODS

Figure 1:
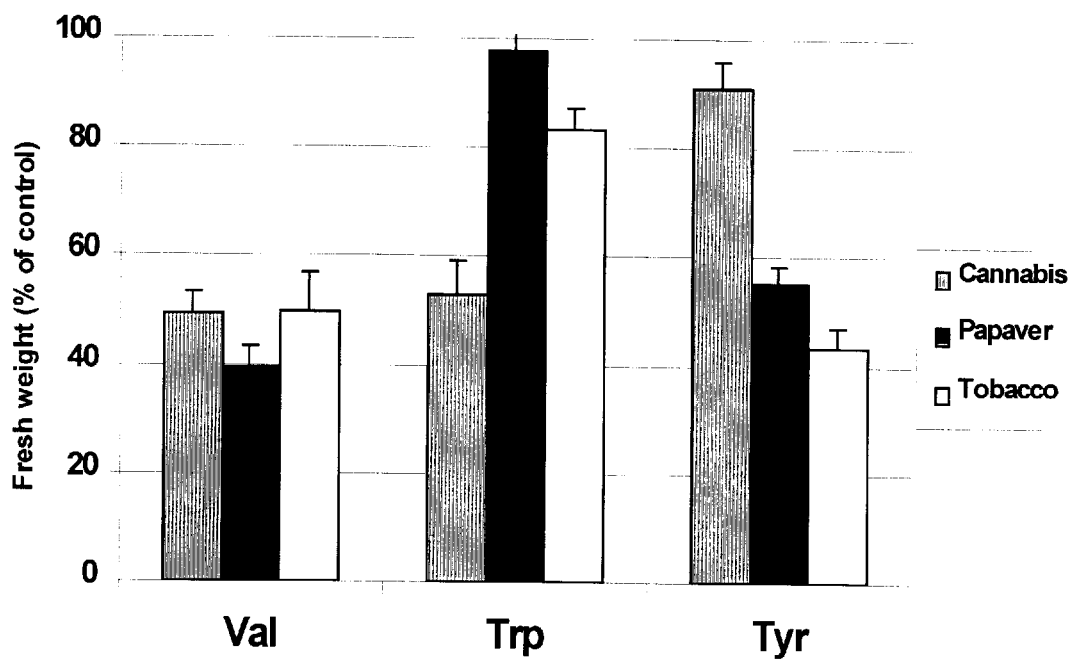
FIG. 1 is a graph showing the growth inhibition of three plant species (cannabis, papaver, and tobacco) caused by application of 0.1 mM of the indicated amino acid.

Fungal cultures. *Fusarium oxysporum* f. sp. cannabis strain Cs95, Fusarium oxysporum f. sp. papaver strains CP3A and 4P-23-1, and *Fusarium oxysporum* f. sp. lycopercici strain 0-1080 were used for mutant selection. Fungal cultures were grown in 250 ml flasks containing 100 ml Potato Dextrose Broth (PDB) (Difco Laboratories, Detroit, Mich.) for 5–7 days at ambient temperature with agitation (200 rpm).

Bacterial cultures. *Pediococcus cerevisiae* (ATCC 8042)—an auxotrophic bacterial strain with strict requirement for valine and other amino acids was used in the standard assay. In an agar medium containing all of the amino acids except one, the microbe will not grow. A bacterial suspension was maintained at −4° C. in 3% glycerol. A single cell colony grown overnight in Lactobacilli MRS broth (MRS) (Difco Laboratories, Detroit, Mich.) was used for assay media preparation.

Amino Acid Toxicity Tests on Plants. Germinated seeds of *Cannabis sativa, Papaver somniferum*, and *Nicotiana tobaccum* were transferred to minimal medium (3% Sucrose (w/v), 1.7 g/l Yeast extract base without amino acids (Difco Laboratories, Detroit, Mich.), 16 g/l Ultrapure Agar (USB, Cleveland, Ohio)) supplemented with increasing concentrations of amino acids. Each amino acid was supplemented at eight concentrations (0 mM, 0.01 mM, 0.1 mM, 0.5 mM, 1 mM, 2 mM, 3 mM, 4 mM), and each treatment was replicated six times. Five pregerminated seeds were placed on each plate, per replication. Plates were incubated at ambient temperature with 12-hour diurnal period for two weeks. The fresh weight per seedling was calculated at the end of the experiment.

Mutant selection. The inhibitory effect of valine and valine analogs was tested against the selected Fusarium spp., using a well zone-diffusion assay on a minimal medium. Seven available valine analogs were tested. The gradient plates were prepared as follows: Minimal media was poured into Petri dishes, then a disk (diameter=10 mm) of the solidified medium was cut out (with number 5 cutter) from the center of the plate and filled with the sterile solution of an analog (0.5 ml of a 1000 :g/ml of analog in sterile distilled $H_2O$). The solution was gradually applied to the well and the plates were allowed to dry and form a gradient under the hood for 24 hours. A Fusarium oxysporum microconidia suspension of $10^7$ sp/ml was obtained by washing a 10–14 day fungal culture grown on minimal medium (with nitrate) with 10 ml of sterile $H_2O$. Five hundred :1 of the spore suspension was thoroughly spread across the plate with a glass rod. These plates were then incubated at 28° C. Resistant colonies observed within inhibition zones were transferred to Minimal agar medium containing 500 :g/ml of a corresponding analog, those that retained the ability to grow, were further evaluated.

Screening Amino Acid Excreting Mutants. The analog resistant colonies of *F. oxysporum* were patched onto Valine assay agar (Difco Laboratories, Detroit, Mich.) seeded with *P. cerevisiae* ($10^8$ cells/liter) (Sands and Hankin, 1974). The plates were incubated for 2–3 days at 28° C. The radius of the halo of Pediococcus growth around the patched mutant was measured and used to estimate the magnitude of valine excretion.

Quantitation of Valine Excretion. Fusarium mutants that excreted valine were grown in minimal medium+$NO_3$ broth for two weeks at ambient temperature with agitation (200 rpm). One ml aliquots of filter sterilized supernatant of each culture were added to 5 ml glass tubes containing 4 ml of valine assay broth inoculated with P. cerevisiae. The tubes were incubated at 37° C. until bacterial growth reached its stationary phase between 24–48 hours. The growth of P. cerevisiae was measured by a Klett apparatus (Klett units). The concentration of valine was then extrapolated from standard curve of valine concentrations (5 $\mu$M, 10 $\mu$M, 20 $\mu$M) versus Pediococcus growth.

Virulence Testing of Pathogens on the Target Host. Cannabis sativa. The virulence of wild-type and mutant strains of *F. oxysporum* f. sp. cannabis were compared in environmental growth chambers (28° C., 19 hours day, 5 hours night). *Cannabis sativa* plants with two—three pairs of true leaves were infested by placing a food based formulation of the wild-type or mutant strains of *F. oxysporum* f. sp. cannabis at the crown of the plant. Control plants were inoculated with autoclaved inoculum. The experiment included five treatments: wild type (Cs95), mutant isolates 4nv (Cs95), 6pa (Cs95), 8pa (Cs95), and a control treatment. The experimental unit consisted of ten individual C. sativa plants grown in 16 cm pots, replicated twice. Plants were watered daily for 2 minutes by an automatic sprinkler system. Plants were evaluated daily for symptoms of vascular wilt. Individual plants were rated for disease severity in the following manner. Individual plants were rated for disease severity on a scale of 1 to 5, where 1=no disease, 2=minor wilting of lower leaves, 3=wilting symptoms observed on 25–50% of leaves, 4=>75% leaves show severe wilting symptoms, 5=dead plant. Disease Average Index (DAI) for each treatment was calculated as =(1n+2n+3n+4n+5n) divided by Total n, where n=number of plants with symptoms from 1 through 5. In addition Disease Incidence Percent (% disease) was estimated for each treatment as =a/b×100%, where a =number of C. sativa plants with severe disease symptoms (from 3 through 5) and b=total number of C. sativa plants per treatment (from 1 through 5). Tissue from plants exhibiting disease symptoms was surface sterilized in 0.5% NaOCI and plated onto 2% water agar amended with antibiotics (hyphal tips were transferred to PDA for purification and identification) and onto a minimal medium supplemented with the corresponding amino acid analog (500 :g/ml).

*Papaver somniferum*. A similar experiment was performed with the wild-type and mutant strains of *F. oxysporum* f. sp. papaver (CP3A and 4p-23-2) in environmental growth chambers (28° C., 19 hours day, 5 hours night). Papaver somniferum plants with three-four pairs of true leaves were soil surface inoculated by placing 0.5 g of food based formulation (CFM) at the base of each plant. Control plants were inoculated with autoclaved inoculum. The experiment included six treatments: 1) wild type (CP3A), 2) valine excretion mutant—1nv (CP3A), 3) wild type 4p-23-2, 4) valine excreting mutant 43pa (4p-23-2), 5) valine excreting mutant 4nv (4p-23-2), and 5) control. An experimental unit consisted of ten individual *P. somniferum* plants, replicated twice. Plants were watered daily for 2 minutes by an automatic sprinkler. Plants were evaluated daily for symptoms of vascular wilt. Individual plants were rated for disease severity as: 1—healthy, 2—slight wilt symptoms (leaf yellowing/discoloring, leaf tips curling), 3—severe wilt symptoms (several leaves wilting, crown discoloring/rot), 4—dead. The disease average index was obtained and data were analyzed in randomized block design with two replications per treatment. Tissue from plants exhibiting disease symptoms was surface sterilized in 0.5% NaOCI and plated onto 2% water agar amended with antibiotics (hyphal tips were transferred to PDA for purification and identification) and onto minimal medium supplemented with the corresponding amino acid analog (500 :g/ml).

Greenhouse Host Range Study. The host range of selected mutants and wild type isolates was evaluated for virulence in environmental growth chambers on the following crop plant species: *Lycopersicon esculentum* (cv. Bonnie Best), *Zea mays* (cv. Sakota), *Triticum aestivum* (cv. Penewawa), *Hordeum vulgare* (cv. Clark), *Phaseolus vulgaris* (cv. Blue Lake Bush), *Festuca arundinaceae* (cv. Apache), and Blue Bunch wheatgrass (*Agropyron spicatum*), *Cucumus sativus* (cv. Straight eight), *Daucus carota* (Burpee), *Gossypium*

*hirsutum* (cv. Stoneville), *Pisum sativum* (cv. Alaska), *Raphanus sativus* (cv. Cherry Bomb), *Melilotus indica* (Burpee). Control plants were inoculated with autoclaved inoculum. Plants were maintained in environmental growth chambers with computer controlled conditions: 28° C. (19 hours day, 5 hours night). One week old plants were inoculated by placing 0.5 g of CFM inoculum at the base of each plant. An experimental unit consisted of five individual plants, replicated twice. Plants were watered daily for 2 minutes by an automatic sprinkler. The plants were evaluated daily for symptoms of vascular wilt. Tissue from plants exhibiting disease symptoms was plated as described earlier in the section. At the end of the experiment, one plant from the wild type isolate treatment was arbitrarily chosen and assessed for the presence of Fusarium by plating plant tissue on Komada's medium (Komada, 1975). Similarly, one arbitrary plant from each treatment with mutant strains was assessed for the presence of Fusarium by plating plant tissue on minimal medium supplemented with the corresponding amino acid analog.

RESULTS

Amino Acid Toxicity Tests on Plants.

Inhibition of plant growth of three plant species (*Cannabis sativa, Papaver somniferum, Nicotiana tobacum*) with various exogenous L-amino acids (valine, tyrosine, phenylalanine, tryptophan and combination of tyrosine and phenylalanine) was studied. The toxicity of increasing concentrations of some exogenously added amino acids resulted in decreased fresh weight per plant/ seedling.

*Cannabis sativa*. Increasing concentrations of exogenous amino acids in minimal media with nitrate as a sole source of nitrogen were inhibitory to normal growth of *C. sativa* seedlings. Inhibitory effects were concentrations of 0.1 mM for all amino acids tested (FIG. 1). The fresh weight of *C. sativa* seedlings grown on the media supplemented with 0.1 mM valine was half of the control *C. sativa* seedlings grown on the media without the amino acid. Phenylalanine at 0.1 mM reduced fresh weight of the seedlings by about 40–45% that of the control. A similar growth inhibition effect was observed on media supplemented with 0.5 mM tryptophan. Tyrosine was less inhibitory than other amino acids tested on *C. sativa* seedlings. The fresh weight was reduced by 25–30% with 1 mM tyrosine. The combination of tyrosine and phenylalanine was more inhibitory than tyrosine alone, but less inhibitory than phenylalanine alone. Complete inhibition of root apical growth of all seedlings was observed at 1 mM–2 mM of any amino acid tested.

*Papaver somniferum*. *Papaver somniferum* seedling grown on media supplemented with 0.1 mM valine were reduced in fresh weight by about 60% as compared to the control seedlings (FIG. 1). Tyrosine 0.1 mM reduced fresh weight of the seedlings by about 40% compared to the control. Phenylalanine and tryptophan were less inhibitory to *P. somniferum* seedling growth than other amino acids tested. Fresh weight was reduced by 20% at 1 mM. Maximum reduction of the fresh weight, 30–40%, was observed starting at 3 mM of phenylalanine or tryptophan. The combination of tyrosine and phenylalanine was more inhibitory than phenylalanine, but less than tyrosine alone.

*Nicotiana tobacum*. Growth inhibition of tobacco seedlings on agar by increasing concentrations of the amino acids was also observed starting at 0.1 mM (FIG. 1). Tyrosine reduced fresh weight of the seedlings by 50–60% at a concentration of 0.1 mM. A similar level of inhibition was observed on agar media supplemented with 0.1 mM valine. Phenylalanine (0.1 mM) and tryptophan (0.1 mM) reduced fresh weight by 20% of control seedlings.

Valine Excreting Mutants

Eight analogs of valine were tested against the pathogen using a well zone-diffusion assay on minimal medium. Six analogs (L-valine hydroxamate, L-valine amide, DL-α-keto-β-methyl valeric acid, L-valinol and L-amino-n-butyric acid) were not inhibitory to any of the strains of *F. oxysporum* tested. Norvaline and penicillamine were inhibitory to *Fusarium oxysporum*. After several days of incubation, mutant colonies appeared within the zones of inhibition on plates inoculated with either *F. oxysporum* f. sp. cannabis or *F. oxysporum* f. sp. papaveris. Resistant colonies were transferred to minimal plates supplemented with 500 :g/ml of the corresponding analog. Colonies capable of wild type growth in the presence of the inhibitory analog were further analyzed for valine excretion.

Valine Excretion.

The resulting analog resistant colonies were screened for their ability to secrete valine. Preliminary data showed that several mutants excreted 10–55 times as much valine as the wild type parent (Table 1). The quantitative analysis showed that the concentration of valine secreted by mutants could be between 20 and 93 $\mu$M in the fungal filtrates, in contrast to the wild type between 0 and 3 $\mu$M of valine.

TABLE 1

Valine Excretion by Wild Type and Analog Resistant Isolates of *Fusarium oxysporum*.

| Isolate | Analog Resistance | Valine Excretion (mg/l) |
|---|---|---|
| Cs95 wild-type | — | 0–0.18 |
| 4nv(Cs95) | Norvaline | 2.84 |
| 6pa(Cs95) | Penicillamine | 2.48 |
| 8pa(Cs95) | Penicillamine | 9.93 |
| CP3A wild-type | — | 0.35 |
| Inv(CP3A) | Norvaline | 3.19 |
| 4p-23-2 wild-type | — | 0–0.18 |
| 44nv(4P-23-2) | Norvaline | 10.83 |
| 45nv(4P-23-2) | — | 4.26 |
| 43pa(4P-23-2) | Penicillamine | 4.61 |
| 4p-23-2 25 pa | Penicillamine | 2.31 |

Pathogenicity Evaluation

*Cannabis saliva*. Virulence of wild type *Fusarium oxysporum* f. sp. cannabis Cs95 and its valine excreting mutants (4nvCs95, 6paCs95, 8paCs95) was evaluated on *Cannabis sativa*. The average disease ratings of the *C. saliva* plants in treatments of all *F. oxysporum* isolates were significantly higher than disease ratings of the control plants (Table 2). The average disease ratings of plants inoculated with *F. oxysporum* mutant isolates 4nv (Cs95), 6pa (Cs95), 8pa (Cs95) were significantly higher than disease ratings of plants inoculated with the parent wild type (Cs95) isolate (p<0.05). The studies conducted in growth chambers showed an increased level of virulence. The wild type strain resulted in 25% control of the target plant, while the mutants showed increased control to 70–90%.

The development of wilt disease symptoms in treated plants was also faster in the case of mutant isolates (Table 2). Cannabis plants inoculated with wild type parent strain were dead or severely wilted in a period of 6–8 weeks, while *C.* saliva plants infested with valine excreting mutants of strain CSs95 showed severe wilt and death in period of 2–3 weeks.

TABLE 2

Disease Severity on C. sativa Plants Inoculated with Valine Excreting Mutants of *Fusarium oxysporum* f. sp. *cannabis* Cs95.

| Isolate | DAI[1] | % disease[2] | Duration[5] |
|---|---|---|---|
| Control[3] | 1.35 a[4] | 0% | 8 weeks |
| wt (Cs95) | 2.40 b | 25% | 6–8 weeks |
| 4nv (Cs95) | 3.75 c | 70% | 2–3 weeks |
| 6pa (Cs95) | 4.45 cd | 90% | 2–3 weeks |
| 8pa (Cs95) | 4.60 d | 90% | 2 weeks |

[1]Disease average index was rated using a 1 (no disease) to 5 (dead plant) rating scale.
[2]Percent Disease was calculated using = a/b × 100, where a- amount of plants with disease symptoms (3–5), and b- total amount of C. sativa plants per treatment (1–5).
[3]Means with the same letter are not significantly different (p ≤ 0.05).
[4]Duration means time lapsed after inoculation until appearance of severe wilt symptoms or death.

The nodes of infested and control plants were plated on minimal media supplemented with 500 mg/l of norvaline. In plants treated with the valine excreting mutant 4nv(Cs95) about 84% of nodes with wilted leaves and 39% of nodes with leaves not showing wilting yielded the pathogen. In plants treated with wild type parent strain, 87% of nodes with wilted leaves and 7.5% of nodes with nonwilted leaves yielded the pathogen. Symptoms of leaf distortion were associated with the presence of the pathogen in vascular tissues of the symptomatic leaf in all plants tested.

*Papaver somniferum*. Pathogenicity evaluation of valine excreting mutant 1nv (CP3A) of *Fusarium oxysporum* f. sp. papaver on *Papaver somniferum* showed increased virulence compared to the wild type parent isolate CP3A (Table 3).

TABLE 3

Disease Severity on *P. somniferum* Plants Grown in Greenhouse Caused by Valine Excreting Mutants of *Fusarium oxysporum* f. sp. *papaver*

| Isolate | DAI[1] | % disease[2] | Duration[5] |
|---|---|---|---|
| Control | 1.1 a[3] | 0% | 2 weeks |
| wt (CP3A) | 1.9 b | 30% | 2 weeks |
| 1nv (CP3A) | 2.8 c | 60% | 2 weeks |
| LSD (0.05) 0.71 | | | |

[1]Disease average index.
[2]Percent Disease was calculated using = a/b × 100, where a- amount of plants with disease symptoms, and b- total amount of *P. somniferum* plants per treatment.
[3]Means with the same letter are not significantly different (p ≤ 0.05).
[5]Duration means time lapsed after inoculation until appearance of severe wilt symptoms or death.

Host Range Study.

Symptoms of Fusarium wilt were observed on *C. sativa* inoculated with the wild type or valine excreting strains of *F. oxysporum* f. sp. cannabis (Table 4). Symptoms were not observed on nonhost plants inoculated with either the wild type or valine excreting strains. *Fusarium oxysporum* f. sp. lycopersici strain 0–1080 incited disease on tomato but did not adversely effect non-host species.

TABLE 4

Incidence of Vascular Wilt on Crop Plant Species Infested Wild-Type and Valine Excreting Mutants of *Fusarium oxysporum* f. sp. *cannabis*.

| Plant spp. | Control | 0–1080 | Cs95 | 4nv(Cs95) | 6pa(Cs95) |
|---|---|---|---|---|---|
| Lycopersicon esculentum | − | + | − | − | − |
| Zea mays | − | − | − | − | − |
| Triticum aestivum | − | − | − | − | − |
| Phaseolus vulgaris | − | − | − | − | − |
| Hordeum vulgare | − | − | − | − | − |
| Festuca arundinaceae | − | − | − | − | − |
| Agropyron spicatum | − | − | − | − | − |
| Cannabis sativa | − | − | ++ | +++ | +++ |
| Cucumus sativus L. | − | − | − | − | − |
| Gossypium L. | − | − | − | − | − |
| Pisum L. | − | − | − | − | − |
| Daucus carota L. | − | − | − | − | − |
| Melilotus L. | − | − | − | − | − |
| Raphanus L. | − | − | − | − | − |

Discussion

*Fusarium oxysporum* Sclecht., a plant pathogenic fungus, is an excellent candidate for biocontrol of weeds ((McCain, 1984; Sands et al. 1997; Boyette et al. 1993; Hildebrand and McCain 1978). There are over ninety known forna speciales of *F. oxysporum*, each attacking one genus or even one species of host plants (Brayford 1993). Newforma speciales are discovered with great frequency, often in association with weedy plant species. Theseforma cause vascular wilts, leading to death of the plants. All are soil borne, survive as chlamydospores, and are capable of growing as saprophytic mycelia on the roots of non-host plants. When the mycelia encounter their host plant, they invade the vascular tissue, stunting or killing their host. *Fusarium oxysporum* generally causes low mortality even under ideal conditions. For example, *F. oxysporum* f. sp. cannabis killed 25% of infested *C. sativa* plants within six weeks in greenhouse studies (Tiourebaev 1999). Mortality rates are similar under field conditions. For annual herbaceous weeds, this is not an effective "knockdown" rate.

The objective of this investigation was to improve, via mutagenesis and selection, *Fusarium oxysporum* as a potential candidate for biological weed control. Described here are mutants that are resistant to toxic analogs of the amino acid valine. Bioassay using growth response in valine assay media (Difco Products) of auxotrophic bacterium *Pediococcus cerevisiae* ATCC 8042 to culture filtrates of mutant strains of *Fusarium oxysporum* showed that these mutants excrete 10–55 times more valine than the wild type parent strain. Semiquantitative analysis showed that the concentration of secreted valine by mutants could be between 20 and 93 $\mu$M in the fungal filtrates, in contrast to wild type between 0 and 3 $\mu$M of valine (Table 4.1).

Increasing concentrations of exogenous valine in minimal media starting at 0.1 mM were inhibitory to normal growth of *Cannabis saliva* seedlings. The inhibitory effect resulted in reduced root system and overall biomass of *C. saliva* seedlings. Fresh weight of *C. saliva* seedlings grown on the media supplemented with 0.1 mM valine was reduced by 50% as compared to that of the control *C. saliva* seedlings.

The pathogenicity studies conducted in growth chambers showed significant differences in the virulence of tested mutant strains of *Fusarium oxysporum* f. sp. cannabis to *C. saliva* as compared to wild type and control treatments (p<0.05). Twenty-five to thirty percent of plants inoculated with wild type strain Cs95 were killed or showed severe wilt symptoms 6- to 8-weeks after inoculation. In comparison mutant strains 4nv(Cs95), 6pa (Cs95) and 8pa (Cs95) killed or caused severe wilt in 70–90% of inoculated plants 2–3weeks after inoculation (Table 4.2). The observed symptoms were similar to the symptoms of "frenching" disease in tobacco incited by isoleucine producing strains of *Pseudomonas flourescens* (Steinberg 1950, 1956; Lucas 1965). Limited host range studies on fourteen plant species did not reveal increased pathogenicity of valine excreting mutants toward non-host plant species Table A1.

A similar approach was used to obtain valine analog-resistant mutants of *Fusarium oxysporum* f. sp. papaveris. The concentration of secreted valine by *Fusarium oxysporum* f. sp. papaver mutants ranged from 4.62 mg/l to 10.83 mg/l compared to 0–0.18 mg/l for the wild type strain (Table 4.1). The pathogenicity evaluation of resulting valine excreting mutants of *Fusarium oxysporum* f. sp. papaver is underway (Table 4.4).

In conclusion, we propose the method of selecting valine excreting mutants of *Fusarium oxysporum* with enhanced pathogenicity as a method of improving virulence of existing *Fusarium oxysporum* mycoherbicides. Also incremental increases in virulence can be made by selection for additional excretion of the same or different amino acid. In addition the resistance of the mutant strains to various amino acid analogs enables the strains thus to be marked for their field release.

References Cited

Adelberg, E. A. 1958. Selection of bacterial mutants which excrete antagonists of antimetabolites. *J Bacteriol.* 76: 326.

Amrhein, N. 1986. Specific inhibitors as probes into the biosynthesis and metabolism of aromatic amino acids. In: The shikimic acid pathway. (Conn, E. E. ed). *Rec. Adv. Biochemistry.* 20: 83–117.

Boyette, C. D., Abbas, H. K., Connick, W. J. Jr. 1993. Evaluation of *Fusarium oxysporum* as a potential bioherbicide for sicklepod (*Cassia obtusifolia*), coffee senna (*C. occidentalis*), and hemp (*Sesbania exaltata*). Weed Sci. 41: 678–681.

Brayford, D. 1993. The identification of Fusarium species. Manual for a workshop held at the International Mycological Institute. Bakeham Lane, Egham, Surrey, U. K. Cab International Bryan, J. K. 1980. Synthesis of the aspartate family and branched-chain amino acids. In: The biochemistry of plants. Acad. Press. New York, London. v 5: 403–452.

Carlson, P. S. 1973. The use of protoplasts for genetic research. *Proc. Nat. Acad. Sci.* 70: 598–602.

Green, C. E., and Phillips, R. L. 1974. Potential selection system for mutants with increased lysine, threonine, and methionine in cereal crops. *Crop Sci.* 14: 827–830.

Hildebrand, D. C., and McCain, A. H. 1978. The use of various substrates for large scale production of *Fusarium oxysporum* f. sp. cannabis inoculum. *Phytopathology* 68: 1099–1101.

Lucas, G. B. 1965. Frenching. In: Diseases of tobacco. The Scarecrow Press. New York & London. pp. 478–485.

Komada, H. 1975. Development of a selective medium for quantitative isolation of *Fusarium oxysporum* from natural soil. *Rev. Plant Prot. Res.* 8: 114–124.

Maiti, S. N., Zink, M, W., and Rank, G. H. 1988. Effect of valine and the herbicide sulfometuron methyl on acetolactate synthase activity in nuclear and plasmid-borne sulfometuron methyl resistant *Saccharomyces cerevisiae* strains.

McCain, A. H., and Noviello, C. 1984. Biological Control of *Cannabis sativa*. Agric. Can. pp. 635–642 Proc. VI Int. Symp. Biol. Contr. Weeds. (E. S. Delfosse, Ed.) Vancouver, Canada.

Relton, J. M., Wallsgrove, R. M., Bourgin, J. P., and Bright, S. W. J. 1986. Altered feedback sensitivity of acethydroxyacid synthase from valine-resistant mutants of tobacco (*Nicotiana tabacum L.*). *Planta* 169: 46–50.

Rosenthal, G. A. 1982. Plant nonprotein amino and imido acids: biological, biochemical and toxicological properties. Acad. Press. New York, London p. 56.

Sands, D. C., Ford, E. J., Miller, R. V., Sally, B. K., McCarthy, M. K., Anderson, T. W., Weaver, M. B., Morgan, C. T., Pilgeram, A. L., and Darlington, L. 1997. Characterization of a vascular wilt of *Erythroxylum coca* caused by *Fusarium oxysporum f. sp. erythroxyli, forma specialis nova*. *Plant Dis.* 81: 501–504.

Sands, D. C., and Hankin, L. 1974. Selecting lysine-excreting mutants of lactobacilli for use in food and feed enrichment. *Appl. Microbiol.* 28 (3): 523–524.

Steinberg, R. A. 1946. A "frenching" response of tobacco seedlings to isoleucine. *Science* 103: 329–330.

Steinberg, R. A., Bowling, J. D., and McMurtrey, J. E. 1950. Accumulation of free amino acids as a chemical basis for morphological symptoms in tobacco manifesting frenching and mineral deficiency symptoms. *Plant Physiol.* 25: 279–288.

Tiourebaev, K. 1999. Virulence and dissemination enhancement of a mycoherbicide. Ph. D. thesis, Montana State University, Bozeman.

Umbarger, E., and Davis, D. 1962. Pathways of amino acid biosynthesis. In: The bacteria. A treatise on structure and function. Academic Press. New York London. v. 3, pp 167–253.

Wu, K., Mourad, G., King, J. 1994. A valine-resistant mutant of *Arabidopsis thaliana* displays an acetolactate synthase with altered feedback control. *Planta.* 192: 249–255.

We claim:

1. An enhanced method of controlling plant growth or propagation, comprising exposing the plant to an amino acid capable of enhancing virulence of a plant pathogen in the presence of the plant pathogen.

2. The method of claim 1, wherein the amino acid is:

(a) applied to the plant; or (b) excreted by a supplemental organism.

3. The method of claim 2, wherein the applied amino acid is sprayed on the plant, dusted on the plant, added to irrigation for the plant, added to growth medium in which the plant is growing, or a combination thereof.

4. The method of claim 1, wherein the amino acid is excreted by the plant pathogen or a supplemental organism and the plant pathogen or the supplemental organism excretes the amino acid:

(a) due to a laboratory-induced mutation;

(b) due to selection for amino acid production;

(c) due to selection for resistance to an amino acid analog; or (d) due to genetic transformation.

5. The method of claim 1, wherein the amino acid is valine.

6. The method of claim 1, wherein the plant pathogen is a bacterium or a fungus.

7. The method of claim 6, wherein the fungus is *Fusarium oxysporum*.

8. The method of claim 1, further comprising co-applying another agent for control of plant growth or propagation.

9. The method of claim 1, where the plant is a weed.

10. The method of claim 9, where the weed is *Cannabis sativa, Papaver somniferu*, or *Nicotiana tobacum*.

11. A method of controlling plant growth or propagation, comprising exposing the plant to an amino acid capable of enhancing virulence of a plant pathogen in the presence of the plant pathogen, wherein the plant pathogen is not auxotrophic for the amino acid.

12. A method of controlling plant growth or propagation, comprising exposing the plant to an amino acid capable of enhancing virulence of a plant pathogen in the presence of the plant pathogen, wherein the plant pathogen is viable in the absence of the amino acid but is not virulent enough to control growth or propagation of the plant.

13. The method of claim 12, wherein the plant pathogen is at least twice as virulent in the presence of the amino acid.

* * * * *

UNITED STATES PATENT AND TRADEMARK OFFICE
CERTIFICATE OF CORRECTION

PATENT NO. : 6,673,746 B1
DATED : January 6, 2004
INVENTOR(S) : Sands et al.

It is certified that error appears in the above-identified patent and that said Letters Patent is hereby corrected as shown below:

Column 3,
Line 39, "1000 :g/ml" should be -- 1000 µg/ml --.
Line 36, "Five hundred :1" should be -- Five hundred microliters --.
Line 40, "500 :g/ml" should be -- 500 µg/ml --.

Column 4,
Line 42, "5) control." should be -- 6) control. --.

Column 6,
Line 17, "500 :g/ml" should be -- 500 µg/ml --.
Table 1, Line 6, "Inv(CP3A)" should be -- 1nv(CP3A) --.
Line 60, "(p<0.05)" should be -- (p≤0.05 --.

Column 7,
Line 2, "CSs95" should be -- Cs95 --.

Column 8,
Line 25, "((McCain," should read -- (McCain, --.
Line 27, "forna" should be -- forma --.
Line 29, "Newforma" should be -- New forma --.
Line 31, "Theseforma" should be -- These forma --.
Line 55, "(Table 4.1)" should be -- (Table 1) --.
Lines 59, 60, 61 and 67, "*saliva*" should be -- *savita* --.

UNITED STATES PATENT AND TRADEMARK OFFICE
CERTIFICATE OF CORRECTION

PATENT NO. : 6,673,746 B1
DATED : January 6, 2004
INVENTOR(S) : Sands et al.

It is certified that error appears in the above-identified patent and that said Letters Patent is hereby corrected as shown below:

<u>Column 9,</u>
Line 1, "(p<0.05)" should be -- (p≤0.05 --.
Line 6, "2-3 weeks" should be -- 2-3 weeks --.
Line 6, "(Table 4.2)." should be -- (Table 2). --.
Line 12, "Table A1" should be -- (Table 4) --.
Line 17, "(Table 4.1)" should be -- (Table 1) --.
Line 19, "(Table 4.4)" should be -- (Table 4) --.
Line 45, "International" should be -- International. --.

Signed and Sealed this

Twenty-eighth Day of September, 2004

JON W. DUDAS
*Director of the United States Patent and Trademark Office*